United States Patent
Tammana et al.

(10) Patent No.: US 12,098,121 B2
(45) Date of Patent: Sep. 24, 2024

(54) METHODS FOR PRODUCING XYLENES WITH LIMITED ETHYLBENZENE PRODUCTION

(71) Applicant: Saudi Arabian Oil Company, Dhahran (SA)

(72) Inventors: Veera Venkata Ramakrishna Tammana, Dhahran (SA); Ke Zhang, Stoneham, MA (US); Sohel Shaikh, Dhahran (SA); Essam A. Al-Sayed, Al-Khobar (SA); Miao Sun, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/165,626

(22) Filed: Feb. 7, 2023

(65) Prior Publication Data

US 2024/0262766 A1   Aug. 8, 2024

(51) Int. Cl.
*C07C 4/12* (2006.01)
*C07C 4/18* (2006.01)

(52) U.S. Cl.
CPC ............... *C07C 4/12* (2013.01); *C07C 4/18* (2013.01); *C07C 2529/44* (2013.01); *C07C 2529/48* (2013.01)

(58) Field of Classification Search
CPC ......... C07C 4/12; C07C 4/18; C07C 2529/44; C07C 2529/48
See application file for complete search history.

(56) References Cited

U.S. PATENT DOCUMENTS

| | | |
|---|---|---|
| 5,942,651 A | 8/1999 | Beech, Jr. et al. |
| 7,393,989 B2 | 7/2008 | Negiz et al. |
| 7,459,413 B2 | 12/2008 | Shen et al. |
| 8,329,973 B2 | 12/2012 | Inui et al. |
| 8,481,443 B2 | 7/2013 | Levin et al. |
| 8,653,315 B2 | 2/2014 | Ali |
| 9,227,181 B2 | 1/2016 | Harris |
| 10,118,163 B1 | 11/2018 | Zhang |
| 2003/0036670 A1* | 2/2003 | Oh ............................ B01J 29/80 585/475 |
| 2018/0361365 A1* | 12/2018 | Jermy .................. B01J 35/1042 |

FOREIGN PATENT DOCUMENTS

WO        9502653 A1    1/1995

* cited by examiner

*Primary Examiner* — Thuan D Dang
(74) *Attorney, Agent, or Firm* — DINSMORE & SHOHL LLP

(57) ABSTRACT

A method for producing one or more of benzene, toluene, or xylene may include contacting a feed stream including $C_{9+}$ alkylaromatic hydrocarbons with a catalyst mixture to form one or more of benzene, toluene, or xylene. The catalyst mixture may include mesoporous zeolite Beta, ZSM-5 zeolite, one or more active metals, and binder material. The feed stream may include $C_{9+}$ alkylaromatic hydrocarbons in an amount of at least 10 wt. %. The weight ratio of mesoporous zeolite Beta to ZSM-5 zeolite may be from 2 to 4.

12 Claims, 2 Drawing Sheets

METHODS FOR PRODUCING XYLENES WITH LIMITED ETHYLBENZENE PRODUCTION

BACKGROUND

Field

This disclosure relates to methods for producing one or more of benzene, toluene, and xylenes and, more specifically, to catalyst compositions utilized in reactions that form one or more of benzene, toluene, and xylenes.

Technical Background

BTX (i.e., benzene, toluene, and xylene isomers) are valuable hydrocarbon products. Many petrochemical products may be produced from BTX, such as polystyrene, nylon, phenolic resins, polyurethane, and polyester. BTX may be recovered from petrochemical refinery products directly, or may be produced from refinery products by further processing. However, it is difficult to produce BTX without also producing other, non-desirable aromatics such as ethylbenzene. For example, ethylbenzene may be very difficult to remove from BTX due to its similar boiling point. As such, there is a continued need for improved methods for producing BTX with limited ethylbenzene production.

BRIEF SUMMARY

According to embodiments described herein, xylenes, as well as toluene and benzene, may be produced by the catalytic reaction of alkyl aromatics having at least 9 carbon atoms (referred to herein as $C_{9+}$ alkyl aromatics). Generally, the BTX may be formed by transalkylation reaction of the $C_{9+}$ alkyl aromatics. It has been discovered that desirable yields of xylene may be produced along with less production of ethylbenzene when ZSM-5 zeolite is utilized in combination with mesoporous zeolite Beta. The presently disclosed methods may utilize a catalyst mixture that includes mesoporous zeolite Beta, ZSM-5 zeolite, active metals, and binder material. In one or more of the embodiments, side production of ethylbenzene may be reduced substantially as compared with other catalysts, such as those that include mesoporous Beta zeolite but do not include ZSM-5 zeolite.

According to one or more embodiments, one or more of benzene, toluene, or xylene may be made by a method that comprises contacting a feed stream comprising $C_{9+}$ alkylaromatic hydrocarbons with a catalyst mixture to form one or more of benzene, toluene, or xylene. The catalyst mixture may comprise mesoporous zeolite Beta, ZSM-5 zeolite, one or more active metals, and binder material. The feed stream may comprise $C_{9+}$ alkylaromatic hydrocarbons in an amount of at least 10 wt. %. The weight ratio of mesoporous zeolite Beta to ZSM-5 zeolite may be from 2 to 4.

Additional features and advantages of the described embodiments will be set forth in the detailed description which follows, and in part will be readily apparent to those skilled in the art from that description or recognized by practicing the described embodiments, including the detailed description which follows, the claims, as well as the appended figures.

BRIEF DESCRIPTION OF THE DRAWINGS

The following detailed description of specific embodiments of the present disclosure can be best understood when read in conjunction with the following drawings, where like structure is indicated with like reference numerals and in which.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Figure 1:
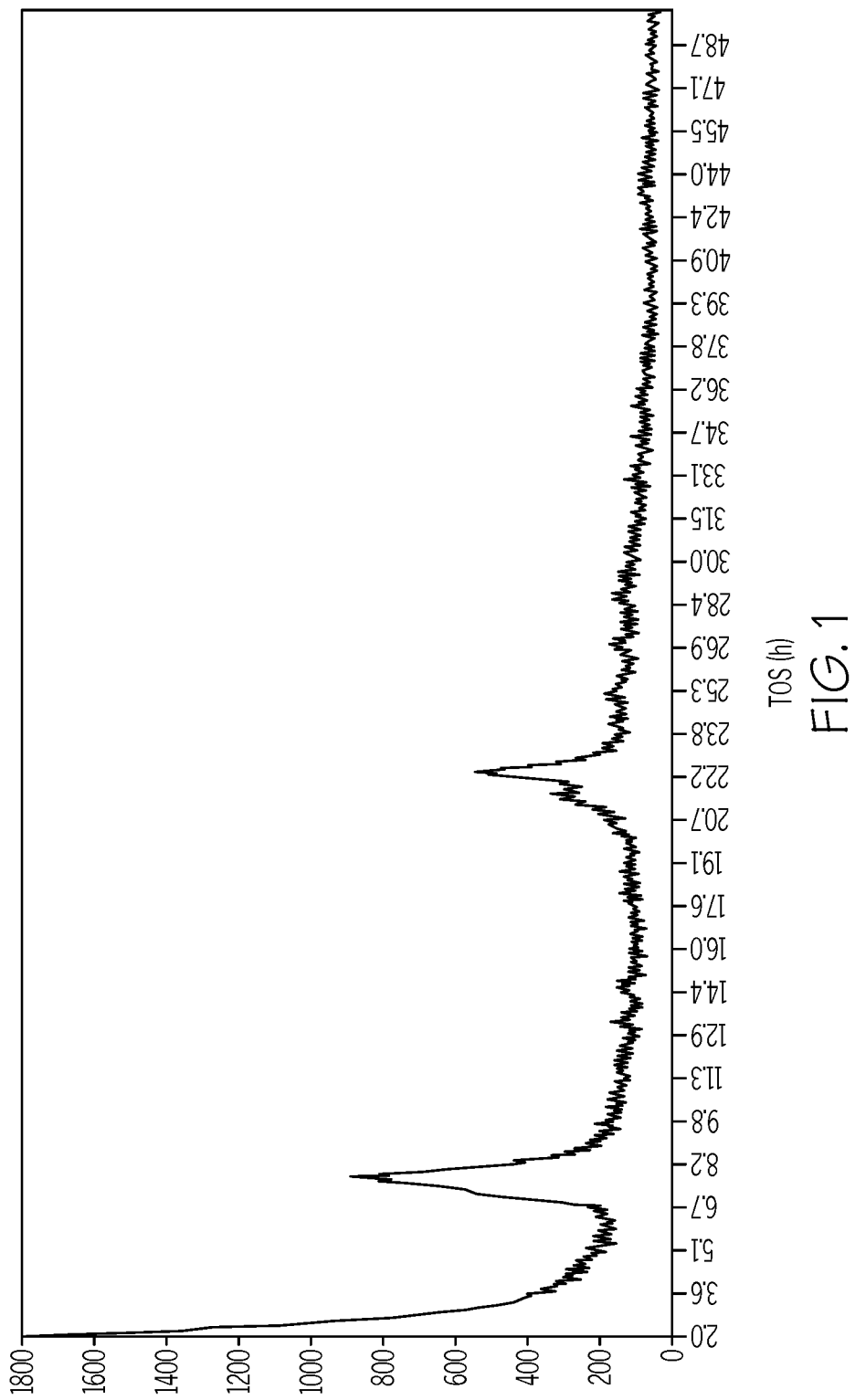
FIG. 1 illustrates an x-ray diffraction (XRD) pattern of mesoporous zeolite Beta, according to one or more embodiments described herein.

Embodiments of the present disclosure are directed to method for producing BTX from $C_{9+}$ alkyl aromatics. Generally, the $C_{9+}$ alkyl aromatics may be introduced into a reactor in a feed stream and contacted by a catalyst mixture that includes at least mesoporous zeolite Beta and ZSM-5 zeolite. Such catalyst is described in detail herein. In one or more embodiments, the feed stream may be gaseous in phase, and the catalyst mixture may be situated in a fixed bed reactor. However, other types of catalyst beds are contemplated.

In one or more embodiments, the feed stream may comprise $C_{9+}$ alkyl aromatics, such as Co to Cn alkyl aromatics. Examples of such hydrocarbons that may be present in the feed stream include propylbenzenes, ethylmethylbenzenes, tetramethylbenzenes, ethyldimethylbenzenes, trimethylbenzenes, or diethylbenzenes, methylpropylbenzenes. In some embodiments, the feed stream is a heavy reformate comprising $C_{9+}$ alkyl aromatics, which is available on the commercial market as a refinery product or intermediate.

In one or more embodiments, the feed stream may comprise $C_{9+}$ alkylaromatic hydrocarbons in an amount of at least 10 wt. %. For example, the feed stream may comprise $C_{9+}$ alkylaromatic hydrocarbons in an amount of at least 10 wt. %, at least 15 wt. %, at least 20 wt. %, at least 25 wt. %, at least 30 wt. %, at least 35 wt. %, at least 40 wt. %, at least 45 wt. %, at least 50 wt. % or even at least 55 wt. %.

In some embodiments, the feed stream may be a heavy reformate stream that comprises toluene. For example, the heavy reformate stream may comprise at least 20 wt. % toluene, at least 30 wt. % toluene, or, for example, from 30 wt. % to 50 wt. % toluene. One example heavy reformate composition is described in the second example which follows. Such an embodiment may include toluene in amounts of, for example, at least 10 wt. %, at least 20 wt. %, or even at least 30 wt. %, such as from 30 wt. % to 50 wt. %. Without being bound by theory, it is believed that the presence of toluene may permit effective transalkylation between benzene and $C_{9+}$ aromatics to form desirable products such as xylenes. However, it should be understood that other process streams may be utilized as feeds in the present embodiments. In additional embodiments, the feed stream may be a recycled portion of the product stream.

In one or more embodiments, the feed stream may be contacted by the catalyst mixture at a temperature of from 50° C. to 600° C. For example, the feed stream may be contacted by the catalyst mixture at a temperature of from 50° C. to 100° C., from 100° C. to 150° C., from 150° C. to 200° C., from 200° C. to 250° C., from 250° C. to 300° C., from 300° C. to 350° C., from 350° C. to 400° C., from 400° C. to 450° C., from 450° C. to 500° C., from 500° C. to 550°

C., from 550° C. to 600° C., or any combination of these ranges. In one embodiment, the feed stream may be contacted by the catalyst mixture at a temperature of from 350° C. to 450° C.

In one or more embodiments, the feed stream may be contacted by the catalyst mixture at a pressure of from 5 bar to 30 bar. For example, the feed stream may be contacted by the catalyst mixture at a pressure of from 5 bar to 10 bar, from 10 bar to 15 bar, from 15 bar to 20 bar, from 20 bar to 25 bar, from 25 bar to 30 bar, or any combination of these ranges. In one embodiment, the feed stream may be contacted by the catalyst mixture at a pressure of from 20 bar to 30 bar.

The liquid hourly space velocity may be from 1/h to 15/h, such as from 1/h to 5/h, from 5/h to 10/h, from 10/h to 15/h, or any combination of these ranges.

In one or more embodiments, one or more components of the feed stream (such as $C_{9+}$ alkyl aromatics) may be transalkylated in the vapor phase. The reaction may be in the presence of hydrogen. The hydrogen may be associated with the feed stream and recycled hydrocarbons in an amount from 0.1 moles to 10 moles of hydrogen per mole of alkylaromatics. This ratio of hydrogen to alkylaromatics is referred to herein as the hydrogen-to-hydrocarbon ratio. The transalkylation reaction may yield a product having mixed xylene content, and further comprises toluene and benzene.

The feed stream to a reaction zone, sometimes referred to herein as a transalkylation reaction zone, may be heated, first by indirect heat exchange against the effluent of the reaction zone, and then further heated to reaction temperature. The feed stream may then be passed through the reaction zone, which may comprise one or more individual reactors. A single reaction vessel having a fixed cylindrical bed of catalyst may be utilized, but other reaction configurations utilizing moving beds of catalyst or radial-flow reactors or fluidized bed may be alternatively employed. Passage of the feed stream through the reaction zone may result in the production of an effluent stream comprising unconverted feed and product hydrocarbons (such as xylene).

In one or more embodiments, following the transalkylation, the transalkylation effluent (sometimes referred to herein as the product stream) may be separated into a light recycle stream, a mixed $C_8$ aromatics product, and a heavy recycle stream. The mixed $C_8$ aromatics stream may comprise, consist essentially of, or consist of Ethylbenzene, p-Xylene, m-Xylene and o-Xylene components, the presence of ethylbenzene in large quantities, which is a co-boiler, in the xylenes stream will pose sever processing problems in their utility or further downstream operations. The ethylbenzene it may be separated using energy intensive separation process to attain the desired mixed xylenes to enhance the xylenes purity and utility.

In embodiments, the ethylbenzene light recycle product stream may be sent for recovery of p-xylene and other valuable isomers. The light recycle stream may be diverted to other uses, such as to benzene and toluene recovery, but alternatively is recycled partially to the transalkylation zone. The heavy recycle stream may include substantially all of the Co and heavier aromatics and may be partially or totally recycled to the transalkylation reaction zone, or removed from the process for disposal or other processing.

As described herein, the catalyst mixture may comprise mesoporous zeolite Beta. As used in this disclosure, "zeolite Beta" refers to zeolite having a *BEA framework type according to the IZA zeolite nomenclature and consisting majorly of silica and alumina, as would be understood by one skilled in the art. The molar ratio of silica to alumina in the zeolite Beta may be at least 10, at least 25, or even at least 100. For example, the molar ratio of silica to alumina in the zeolite Beta may be from 5 to 500, such as from 25 to 300.

Zeolites generally comprise an ordered microporous structure. The mesoporous zeolite Beta, as described herein, in addition to micropores, comprises mesopores. As used herein a "mesoporous zeolite" refers to a zeolite which includes mesopores, and may have an average pore size of from 2 to 50 nm. The presently disclosed mesoporous zeolites may have an average pore size of greater than 2 nm, such as from 4 nm to 16 nm, from 6 nm to 14 nm, from 8 nm to 12 nm, or from 9 nm to 11 nm. In some embodiments, the majority of the mesopores may be greater than 8 nm, greater than 9 nm, or even greater than 10 nm. The mesopores of the mesoporous zeolites described may range from 2 nm to 40 nm, and the median pore size may be from 8 to 12 nm. Average pore size, as well as other porosity characteristics of a material may be tested by Ar adsorption and evaluated by Brunauer-Emmett-Teller ("BET") analysis methods, as would be understood by those skilled in the art.

In one or more embodiments, the amount of mesoporous zeolite Beta relative to the total weight of the catalyst mixture may be from 40 wt. % to 60 wt. %. For example, the amount of mesoporous zeolite Beta relative to the total weight of the catalyst mixture may be from 40 wt. % to 44 wt. %, from 44 wt. % to 48 wt. %, from 48 wt. % to 52 wt. %, from 52 wt. % to 56 wt. %, from 56 wt. % to 60 wt. %, or any combination of these ranges.

Without being bound by any particular theory, it is believed that the mesoporosity of the Beta zeolite accommodates the relatively large $C_{9+}$ aromatic molecules present in, for example, reformates. It is believed that the mesoporosity allows molecules to have a relatively high degree of diffusion and mass transport, which facilitates transalkylation reactions and produces mixed xylenes.

In one or more embodiments, the catalyst mixture may comprise ZSM-5 zeolite. As used in this disclosure, "ZSM-5" generally refers to zeolites having an MFI framework type according to the IZA zeolite nomenclature and consisting majorly of silica and alumina, as is understood by those skilled in the art. ZSM-5 refers to "Zeolite Socony Mobil-5" and is a pentasil family zeolite that can be represented by the chemical formula $Na_nAl_nSi_{96-n}O_{192} \cdot 16H_2O$, where 0<n<27. According to one or more embodiments, the molar ratio of silica to alumina in the ZSM-5 may be at least 5. For example, the molar ratio of silica to alumina in the ZSM-5 zeolite may be at least 10, at least 12, or even at least 30, such as from 5 to 30, from 12 to 30, from 5 to 80, from 5 to 300, from 5 to 1000, or even from 5 to 1500. Examples of suitable ZSM-5 zeolite include those commercially available from Zeolyst International, such as CBV2314, CBV3024E, CBV5524G, and CBV28014, and from TOSOH Corporation, such as HSZ-890 and HSZ-891.

In one or more embodiments, the amount of ZSM-5 zeolite relative to the total weight of the catalyst mixture may be from 5 wt. % to 25 wt. %. For example, the amount of ZSM-5 zeolite relative to the total weight of the catalyst mixture may be from 5 wt. % to 10 wt. %, from 10 wt. % to 15 wt. %, from 15 wt. % to 20 wt. %, from 20 wt. % to 25 wt. %, or any combination of these ranges.

In one or more embodiments, the weight ratio of mesoporous zeolite Beta to ZSM-5 zeolite is from 2 to 4. For example, the weight ratio of mesoporous zeolite Beta to ZSM-5 zeolite is from 2 to 2.2, from 2.2 to 2.4, from 2.4 to 2.6, from 2.6 to 2.8, from 2.8 to 3, from 3 to 3.2, from 3.2 to 3.4, from 3.4 to 3.6 from 3.6 to 3.8, from 3.8 to 4, or any combination of these ranges. Without being bound by theory, it is believed that this ratio affects the xylene yield, where mixtures outside of this range may have less xylene yield.

Without being bound by any particular theory, it is believed that the incorporation of ZSM-5 zeolite into the catalyst mixture results in synergistic effects leading to enhanced catalystic performance. In particular, it is believed that using the catalyst mixtures described herein lowers the formation of heavy molecules during the course of reaction. Production of heavy molecules makes the catalyst more prone for coking, leading to reduced lifetime.

Moreover, without being bound by theory, it is believed that the addition of ZSM-5 increases the benzene purity, which is an important factor, as benzene purity is very important aspect as the quality specification for benzene and will affect the downstream operations where benzene is processed. Impurities around benzene add additional load on the process to purify the benzene for further downstream operations after transalkylation.

In one or more embodiments, the selection of the amount of ZSM-5 utilized may affect mixed xylene yield.

In one or more embodiments, the catalyst mixture may comprise one or more binder materials, such as alumina-containing compounds or silica-containing compounds (including compounds containing alumina and silica). As used in this disclosure, "binder materials" refer to materials which may serve to "glue" or otherwise hold zeolite and the matrix together in the microsphere. It may improve the attrition resistance of the catalyst particle. For example, the binder material may comprise alumina (such as amorphous alumina), silica-alumina (such as amorphous silica-alumina), or silica (such as amorphous silica). In one or more embodiments the binder material may comprise or consist of Cataloid AP-3, commercially available from Catalysts & Chemicals Industries Co., Ltd (CCIC), Japan. According to embdodiments, at least 50 wt. % of the binder material may be alumina.

In one or more embodiments, the amount of binder material relative to the total weight of the catalyst mixture may be from 20 wt. % to 45 wt. %. For example, the amount of binder material relative to the total weight of the catalyst mixture may be from 20 wt. % to 25 wt. %, from 25 wt. % to 30 wt. %, from 30 wt. % to 35 wt. %, from 35 wt. % to 40 wt. %, from 40 wt. % to 45 wt. %, or any combination of these ranges.

In one or more embodiments, the catalyst mixture comprises one or more active metals. The active metals may be selected from molybdenum, platinum, nickel, cobalt, or combinations thereof. In one or more embodiments, the amount of active metals relative to the total weight of the catalyst mixture may be from 1 wt. % to 10 wt. %. For example, the amount of active metals relative to the total weight of the catalyst mixture may be from 1 wt. % to 2 wt. %, from 2 wt. % to 3 wt. %, from 3 wt. % to 4 wt. %, from 4 wt. % to 5 wt. %, from 5 wt. % to 6 wt. %, from 6 wt. % to 7 wt. %, from 7 wt. % to 8 wt. %, from 8 wt. % to 9 wt. % from 9 wt. % to 10 wt. %, or any combination of these ranges. Any single one of the named active metals may be present in the amounts described herein, or their combinations may be present in the amounts described herein.

In one or more embodiments, to form the catalyst mixture, the binder material, ZSM-5 zeolite, and mesoporous zeolite Beta may be mixed to form extrudates, such as pellets, cylinders, or the like. The extrudate may be loaded with the active metal by incipient wet impregnation, and dried and calcined.

The embodiments of the presently described catalyst mixtures may limit yield of ethylbenzene, which may be desirable since it is generally a lower value product and is difficult to separate from the other higher value products such as, for example, xylenes. Generally, xylene and ethylbenzene are produced in a competition during the processing of heavy aromatic feeds. While ethylbenzene production cannot generally be eliminated completely, the presently disclosed methods allow for minimal ethylbenzene formation. At the same time, according to some of the presently disclosed embodiments, do not significantly lower, or lower at all, the yield of xylene. This is beneficial since the boiling points of ethylbenzene and xylene are similar, making separation difficult.

In one or more embodiments, the product stream that is formed, which may include xylene, may have relatively small amounts of ethylbenzene, such as less than or equal to 0.5 wt. %, less than or equal to 0.4 wt. %, less than or equal to 0.3 wt. %, or even less than or equal to 0.2 wt. %.

Appendix A—Preparation of Example Mesoporous Zeolite Beta

Described now are embodiments of methods of producing mesoporous zeolite Beta, sometimes referred to herein as hierarchical mesoporous zeolite Beta. However, it should be understood that other methods may be utilized to produce mesoporous zeolite Beta that are functional in the context of the presently described catalyst mixtures.

The method comprises providing a parent zeolite Beta with a silicon to aluminum ratio of at least 5. The method further comprises, mixing the parent zeolite Beta with an aqueous metal hydroxide solution and heating the parent zeolite Beta and aqueous metal hydroxide mixture to temperatures greater than or equal to 100° C. to produce the hierarchical mesoporous Beta zeolites having and average pore size greater than 8 nm. In embodiments, the hierarchical mesoporous Beta zeolites are produced without a templating agent or pore-directing agent.

In one embodiment, the method may include a step of providing parent Beta zeolites. The step of providing parent Beta zeolites may include process such as, by way of non-limiting example, synthesizing the microporous parent Beta zeolites or directly acquiring the parent Beta zeolites from another source. It should be understood that multiple methods known in the art may be available to synthesize parent Beta zeolites. In one embodiment, the step of providing parent Beta zeolites includes providing a colloidal mixture comprising parent Beta zeolites, silica, alumina, and water.

In one or more embodiments, a method for producing hierarchical mesoporous Beta zeolites may further comprise mixing the parent Beta zeolites with an aqueous metal hydroxide solution. The aqueous metal hydroxide solution may include a single metal hydroxide species, or may be a combination of two or more metal hydroxide chemical species. In one embodiment, the aqueous metal hydroxide solution comprises at least one alkali metal hydroxide, at least one alkali earth metal hydroxide, or combinations thereof. In other embodiments, the aqueous metal hydroxide solution may comprise LiOH, NaOH, KOH, RbOH, $Mg(OH)_2$, $Ca(OH)_2$, $Sr(OH)_2$, $Ba(OH)_2$, or combinations thereof. In some additional embodiments, ammonium hydroxide may be utilized. Without being limited by theory, it is believed the mixing step evenly disperses the parent Beta zeolites and aqueous metal hydroxide solution. Mixing may comprise stirring, swirling, vortexing, shaking, sonicating, homogenizing, blending, similar processes, or combinations thereof.

In one or more embodiments, the aqueous metal hydroxide solution has a metal hydroxide concentration from 0.01 moles per liter (M) to 10 M. In other embodiments, the aqueous metal hydroxide solution has a concentration from 0.01 M to 5 M; 0.01 M to 3 M; 0.01 M to 1 M; 0.05 M to 1 M; 0.05 M to 0.8 M; 0.05 M to 0.5 M; or 0.1 M to 0.4 M. In one or more embodiments, the parent Beta zeolite and aqueous metal hydroxide mixture has a pH greater than or equal to 12. In other embodiments, the parent Beta zeolite and aqueous metal hydroxide mixture has a pH greater than or equal to 13; from 12 to 14; or from 13 to 14.

In one or more embodiments, a method for producing hierarchical mesoporous Beta zeolites may further comprise heating the parent Beta zeolite and aqueous metal hydroxide mixture. In embodiments, the heating may occur at temperatures greater than or equal to 100° C. In other embodiments, the heating step may occur at temperatures from 100° C. to 550° C. For example, the heating step may occur at temperatures from 100° C. to 150° C.; from 150° C. to 200° C.; from 200° C. to 250° C.; from 250° C. to 300° C.; from 300° C. to 350° C.; from 350° C. to 400° C.; from 400° C. to 450° C.; from 450° C. to 500° C.; from 500° C. to 550° C.; or any combination of these ranges. In one or more embodiments, the parent Beta zeolite and aqueous metal hydroxide mixture is heated for a time interval of greater than or equal to 1 hour. In other embodiments, the parent Beta zeolite and aqueous metal hydroxide mixture is heated for a time interval of from 1 hour to 16 hours; from 4 hours to 16 hours; from 16 hours to 48 hours; from 16 hours to 30 hours; from 16 hours to 24 hours; from 18 hours to 48 hours; from 18 hours to 30 hours; from 18 hours to 24 hours; or from 24 hours to 48 hours.

In one or more embodiments, a method for producing hierarchical mesoporous Beta zeolites produces hierarchical mesoporous Beta zeolites with an average pore size greater than 8 nm. Pore size can be measured by Barrett-Joyner-Halenda (BJH) analysis. BJH analysis measures the amount of gas that detaches from a material at 87 K over a series of pressures. Using the Kelvin equation, of the amount of argon adsorbate removed from the pores of the material together with the relative pressure of the system, can calculate the average pore size of the sample. In embodiments, the method produces hierarchical mesoporous Beta zeolites with an average pore size from 8 nm to 25 nm; from 8 nm to 20 nm; from 10 nm to 25 nm; from 10 nm to 20 nm; from 12 nm to 25 nm; from 12 nm to 20 nm; from 8 nm to 18 nm; from 8 nm to 16 nm; or from 12 nm to 18 nm.

Non-Local Density Functional Theory (NLDFT) method can measure the total pore volume of the mesoporous material with the desorption data. The NLDFT method was designed to take into account the rough surface area of crystalline silica materials. In embodiments, the method produces hierarchical mesoporous Beta zeolites with a total pore volume greater than or equal to 0.35 cubic centimeters per gram ($cm^3/g$); greater than or equal to 0.4 $cm^3/g$; greater than or equal to 0.45 $cm^3/g$; or even greater than or equal to 0.5 $cm^3/g$.

In conventional hierarchical mesoporous Beta zeolite production methods, if maintaining the crystallinity of microporous Beta zeolites is desired, then templating agents or pore-directing agents are required. Templating agents may be calcined with the zeolite precursor at temperatures greater than or equal to 300° C. for a time intervals of at least 1 hour. After calcination, the templating agents may be burned off the zeolite. Templating agents of conventional hierarchical mesoporous Beta zeolite production methods may be organic or in organic in nature. Templating agents may include, by way of non-limiting example, hydrocarbon polymers, nitrogen doped hydrocarbon polymers, tetraethylammonium hydroxide, imethoxsilylpropyldimethyloctadecyl ammonium chloride, tetrapropyl ammonium hydroxide, cetyltrimethylammonium bromide, or combinations thereof. In embodiments, the hierarchical mesoporous Beta zeolites are produced without templating agents.

In conventional "top-down" hierarchical mesoporous Beta zeolite production methods, pore-directing agents may be incorporated into the precursor zeolite solution and calcined at temperatures greater than or equal to 300° C. for a time interval of at least 1 hour. Pore-directing agents of conventional top-down hierarchical mesoporous Beta zeolite production methods may include cationic surfactants and non-ionic surfactants. Cationic surfactant pore-directing agents may include, by way of non-limiting example, dodecyltrimethylammonium, cetyltrimethylammonium, propyltrimethylammonium, tetraethylammonium, tetrapropylammonium, octyltrimethylammonium, or combinations thereof. Non-ionic surfactant pore-directing agents may include, by way of non-limiting example, monoamines, polyamines, or combinations thereof. In embodiments, the hierarchical mesoporous Beta zeolites are produced without pore-directing agents. In one or more embodiments, mesopores are created by mixing parent zeolite Beta with an aqueous metal hydroxide and heating the mixture in a teflon lined autoclave. The mixture is heated to temperatures greater than those conventionally used in "top-down" synthesis at an autogenous pressure. In the alkaline solution, under the elevated pressure and temperature, mesopores form within the Beta zeolites.

Without being limited by theory, it is believed that upon contacting the zeolite during the heating process, the alkaline solution creates the mesopores by preferentially extracting silicon from the zeolite framework (also known as desilication). Further, when the temperature is above 100° C. and the pressure is above ambient atmospheric pressure, the synthetic conditions become similar as the conventional bottom-up approach that favors crystallization of zeolites. During this process, the appropriate amounts of aluminum are critical in achieving hierarchical mesopore formation while preserving zeolite crystallinity. The existence of aluminum in the zeolite framework prevents excessive silicon extraction by the alkaline solution and maintains a zeolite framework with locally-desilicated area that can be recrystallized at the synthetic hydrothermal conditions. Therefore, the crystallinity of the resulting mesoporous zeolites can be preserved during the formation of mesopores.

Crystallinity is a relative property that is generally more relevant in "top-down" zeolite synthesis methods, since this approach starts with parent microporous zeolites as reference samples for direct comparison. It measures how well the acidic sites, that is, the catalytic sites are being preserved in the process of creating mesopores. So, for example, in a conventional "top-down" zeolite synthesis, the crystallinity of the chemically eroded mesoporous zeolite is compared with that of the starting microporous zeolite. The crystallinity of two materials may be compared by XRD. If a parent zeolite exhibits certain XRD peaks, a mesoporous zeolite produced from the parent zeolite with preserved crystallinity exhibits the same peaks with comparable peak intensities. Additionally, crystallinity may be measured by $NH_3$-TPD. In $NH_3$-TPD, the desorption of ammonia from a material is measured over a range of temperatures. If a produced mesoporous zeolite has a similar temperature of maximum desorption as the parent zeolite, then the acidity and crystallinity were deemed as preserved.

Example 1—Formation of Mesoporous Zeolite Beta

Mesoporous zeolite Beta was produced and characterized. 22.2 grams of zeolite Beta (HSZ-931 HOA) with SAR of 28 was procured from TOSOH Chemical Company, Japan. The zeolite Beta was dispersed in 600 ml of 0.2 M aqueous solution of sodium hydroxide stirred for 30 minutes in a one-liter beaker and transferred into a Teflon lined hydrothermal reactor and subjected to desilication at 150° C. for 21 hours. The obtained solid was washed thoroughly to remove residual sodium cations. The pure white solid was dried at 100° C. for 5 hours until moisture free and calcined at 550° C. for 5 hours at a ramp of 5° C./min. The obtained zeolite powder had SAR of 20, average pore size of about 10 nanometers, with peak mesopore size in the range of 20-25 nanometers and total pore volume of 0.59 cc/g. Then the obtained mesoporous zeolite Beta was ion exchanged three times with ammonium nitrate 0.8 Molar aqueous solution at 80° C. for 2 hours and dried at 100° C. for 5 hours until moisture free (10 ml of solution for 1 g of zeolite powder). The obtained mesoporous zeolite Beta was further treated with 0.2 molar nitric acid at 80° C. for 2 hours to dealuminate and manipulate the acidity. The dealuminated zeolite Beta were ion-exchanged with 0.8 M $NH_4NO_3$ aqueous solution at 80° C. for 2 hours and then dried and calcined at 550° C. for 5 hours. The physical characterization of the formed hierarchical zeolite Beta is shown in Table I. BET analysis was unitlzed to gather the data in Table I, where da is average diameter of the mesopores, $S_{BET}$ is the total surface area, $S_{Ext}$ is the external surface area, $V_{total}$ is the total pore volume, $V_{mic}$ is the micropore volume, and $T_{max}$ is the maximum temperature for the $NH_3$-TPD characterization.

TABLE I

| $SiO_2/Al_2O_3$ | $d_a$ (nm) | $S_{BET}$ (m²/g) | $S_{ext}$ (m²/g) | $V_{mic}$ (cc/g) | $V_{total}$ (cc/g) | Total acidity (mmol/g) | $T_{max}$ (° C.) |
|---|---|---|---|---|---|---|---|
| 50 | 9.9 | 608 | 197 | 0.27 | 0.59 | 0.54 | 347 ± 3 |

Example 2—Formation of Mixed Zeolite Catalyst

Figure 2:
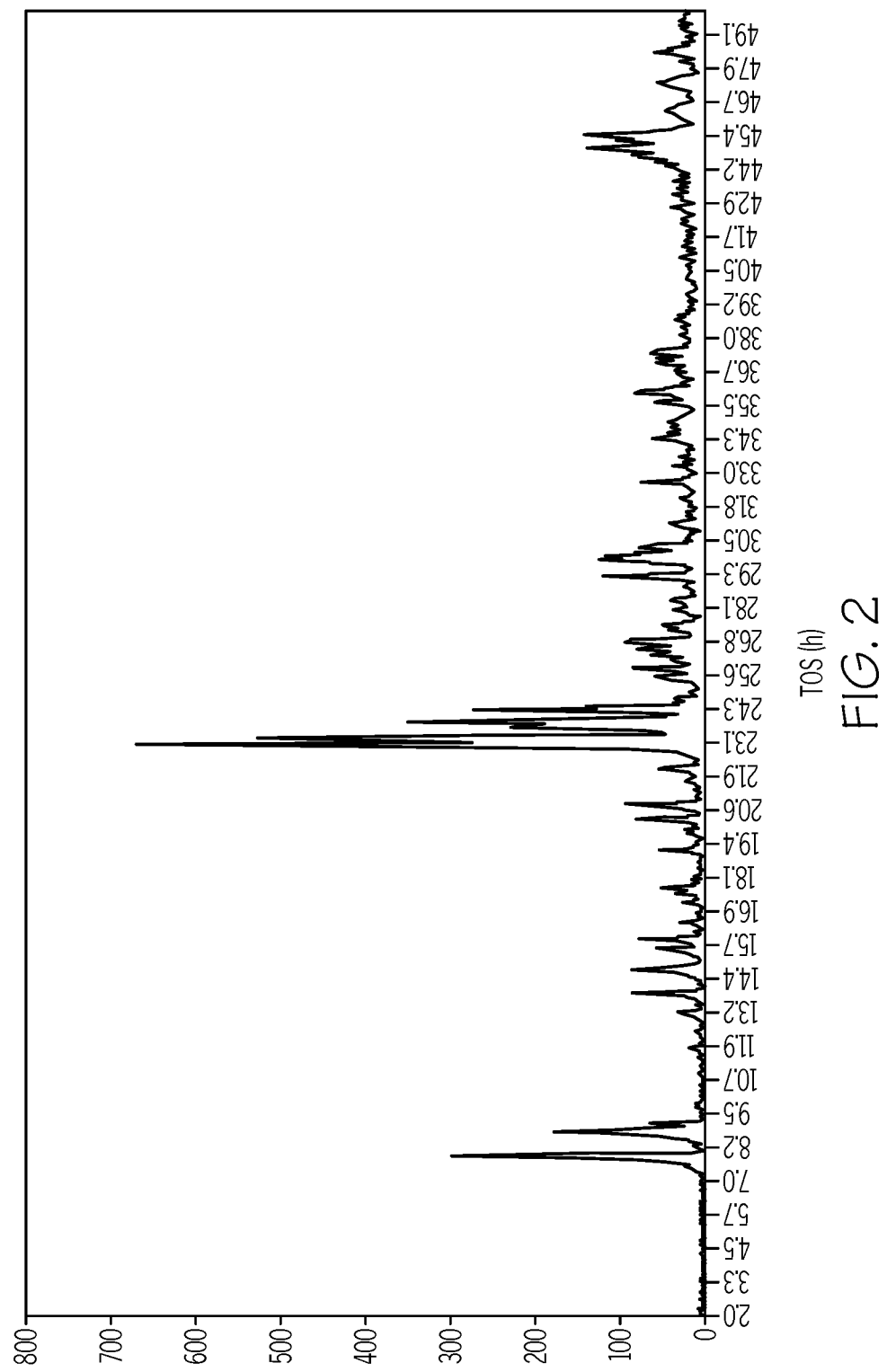
FIG. 2 is illustrates an x-ray diffraction (XRD) pattern of ZSM-5 zeolite, according to one or more embodiments described herein.

A catalyst including the Example 1 zeolite and ZSM-5 was produced. 3 g of the mesoporous zeolite Beta of Example 1 and 1 g ZSM-5 were physically mixed uniformly. FIG. 1 shows the X-ray diffraction pattern for the mesoprous zeolite Beta, and FIG. 2 shows the X-ray diffraction pattern of the ZSM-5 zeolite. This zeolite composite mixture was blended with alumina binder (Cataloid AP-3, obtained from CCIC, Japan) by mixing 67 wt. % composite zeolite and 33 wt. % alumina binder to make cylindrical extrudes. the weight ratio was 50.25 wt. % mesoporous zeolite Beta to 16.75 wt. % ZSM-5 to 33 wt. % alumina binder. These extrudes were loaded with 4 wt. % of molybdenum metal in the form of Ammonium molybdate tetrahydrate through wet impregnation technique, dried at 80° C. for 10 h and then calcined at 450° C. for 5 h.

Comparative Example A—Formation of Single Zeolite Catalyst

A catalyst mixture was prepared similarly to that of Example 2, but did not include any ZSM-5 zeolite. Specifically, the ammoniated mesoporous zeolite Beta of Example 1 (3.35 g) was mixed with 1.65 g of alumina binder (Cataloid AP-3, obtained from CCIC, Japan) to make cylindrical extrudes. Thus, the weight ratio was 67 wt. % mesoporous zeolite Beta to 33 wt. % alumina binder. These extrudes were loaded with 4 wt. % of molybdenum metal in the form of ammonium molybdate tetrahydrate through wet impregnation technique, dried at 80° C. for 10 h and then calcined at 450° C. for 5 h.

Example 3—Catalyst Performance

The catalysts of Example 2 and Comparative Example A were tested for de-alkylation/transalkylation catalytic activity. The catalysts were tested in a fixed bed micro reactor using industrial heavy reformate feedstock using a bench top fixed bed reactor with liquid product collection.

The procedure used for determination of catalytic activity consisted of loading a vertical reactor with 2.0 ml (1 gram) of the catalyst in the middle of reactor together with inert silicon carbide in the lower and upper parts of the reactor. The total volume of the reactor was 20 ml. The catalyst was activated and reduced under 50 ml/min flow of pure hydrogen gas at 450° C. and was kept at this temperature for 2 hours. Then, the pressure of the reactor was increased to 20 bar and the flow of feedstock was started at 4.8 ml/h. The reaction was allowed to run 5 hours at this temperature before collecting the product sample and was further run for 50 hours without loss of activity before termination. Feed and product compositions were tested using gas chromatography.

The feedstock utilized was a heavy reformate having the composition of Table II.

TABLE II

| Major Hydrocarbons | Amount (wt. %) |
|---|---|
| Toluene | 39 |
| p-Xylene | 0.32 |
| m-Xylene | 0.02 |
| o-Xylene | 1.11 |
| n-Propylbenzene | 1.21 |
| p + m Methylethylbenzene | 9.40 |
| 1, 3, 5 Trimethylbenzene | 8.35 |
| o-MethylEthylbenzene | 2.63 |
| 1, 2, 4, Trimethylbenzene | 25.14 |
| 1, 2, 3 Trimethylbenzene | 4.11 |
| Total C7 Components | 39 |
| Total C8 Components | 1.5 |
| Total C9 Components | 50.84 |
| Total C10 and above Components | 8.66 |

The product streams produced by utilizing the catalyst of Example 2 with varying ratios of mesoporous zeolite Beta and ZSM-5 zeolite, as well as a commercially available zeolite Beta and the mesoporous zeolite Beta (without ZSM-5 zeolite) of Comparative Example A are provided in Table III. In Table III, the commercially available zeolite Beta catalyst is HSZ-940 (Commercially available from Tosoh) with 70 wt. % bounded with 30 wt. % alumina and loaded with 4 wt. % Molybdenum. The Comparative Example A catalyst was mesoporous Beta zeolite 70% bounded with 30% alumina and loaded with 4 wt. % Molybdenum. The Example 2 catalysts shown in Table II had varying amounts of ZSM-5. One sample was a mix of 75 wt. % mesoporous Beta and 25 wt. % ZSM-5 bounded with 30 wt. % alumina and loaded with 4 wt. % Molybdenum (total zeolite components are 70% of the finished catalyst). Another sample was a mix of 50 wt. % mesoporous Beta and 50% ZSM-5 bounded with 30 wt. % alumina and loaded with 4 wt. % Molybdenum (total zeolite components are 70% of the finished catalyst). Another sample was a mix of 25% mesoporous Beta and 50 wt. % ZSM-5 bounded with 30 wt. % alumina and loaded with 4 wt. % Molybdenum (total zeolite components are 70 wt. % of the finished catalyst).

TABLE III

|  | Commercially Available zeolite Beta (microporous) | | Comparative Example A (Mesoporous Beta only) | | Example 2 Catalyst with 25% ZSM-5 | | Example 2 Catalyst with 50% ZSM-5 | | Example 2 Catalyst with 75% ZSM-5 | |
|---|---|---|---|---|---|---|---|---|---|---|
| Temperature | 375° C. | 400° C. | 375° C. | 400° C. | 375° C. | 400° C. | 375° C. | 400° C. | 375° C. | 400° C. |
| Xylene wt % | 33.28 | 34.51 | 34.14 | 35.47 | 35.24 | 36.12 | 27.36 | 31.19 | 26.52 | 29.48 |
| Benzene Yield | 3.42 | 4.10 | 3.40 | 4.16 | 4.57 | 5.25 | 4.14 | 5.16 | 4.98 | 6.24 |
| Lights Yield [wt %] | 3.65 | 5.21 | 3.51 | 5.06 | 5.63 | 6.66 | 5.70 | 7.03 | 6.33 | 7.80 |
| Ethylbenzene in C8 Pool | 4.50 | 3.35 | 4.46 | 3.22 | 1.62 | 0.75 | 1.53 | 0.68 | 1.35 | 0.76 |
| Benzene Purity | 98% | 98% | 98% | 98% | 99% | 100% | 100% | 100% | 100% | 100% |
| C10+ Yield [wt %] | 6.56 | 5.43 | 6.68 | 5.49 | 4.22 | 3.66 | 4.90 | 3.96 | 4.48 | 3.76 |
| Conversion TMB | 59.62 | 71.48 | 47.25 | 48.47 | 86.39 | 93.81 | 86.00 | 94.29 | 89.37 | 94.73 |
| Conversion MEB | 46.43 | 47.90 | 60.40 | 73.21 | 45.88 | 48.16 | 40.22 | 46.53 | 39.98 | 47.31 |
| Conv C9+ | 56.36 | 60.31 | 56.98 | 61.07 | 63.06 | 66.19 | 59.46 | 65.25 | 60.20 | 65.88 |

As is shown in the data of Table III, xylene yield was reasonably constant across the examples. However, the catalyst of Example 2 produced significantly less ethylbenzene than the catalysts of Comparative Example A and the commercially available zeolite Beta. Additionally, increased amounts of benzene were observed in some examples where Example 2 catalyst was used. In particular, mixed xylene yields were found to be highest for the Example 2 Catalyst with 25% ZSM-5, which is a combination of 25% ZSM-5 and 75% mesoporous Beta which has resulted in 36.12 wt. % compared other catalyst formulations. However, even with increased mixed xylene yield, ethylbenzene formation was limited in this example.

Additionally, from Table III it can be seen that the commercial Beta zeolite has produced 5.43 wt. % of heavy C10+ products and mesoporous beta alone produces 5.49 wt. % of heavy C10+ but the formulations with ZSM-5 mix produced almost 40% less heavy products.

The present specification includes technical aspects. One aspect is a method for producing one or more of benzene, toluene, or xylene, the method comprising: contacting a feed stream comprising $C_{9+}$ alkylaromatic hydrocarbons with a catalyst mixture to form one or more of benzene, toluene, or xylene, the catalyst mixture comprising: mesoporous zeolite Beta; ZSM-5 zeolite; one or more active metals; and binder material; and wherein: the feed stream comprises $C_{9+}$ alkylaromatic hydrocarbons in an amount of at least 10 wt. %; and the weight ratio of mesoporous zeolite Beta to ZSM-5 zeolite is from 2 to 4.

Another aspect includes any of the other aspects, wherein a product stream is formed by the contacting of the feed stream with the catalyst mixture, and wherein the product stream comprises less than or equal to 0.5 wt. % ethylbenzene.

Another aspect includes any of the other aspects, wherein the weight ratio of mesoporous zeolite Beta to ZSM-5 zeolite is from 3 to 4.

Another aspect includes any of the other aspects, wherein the feed stream is a heavy reformate.

Another aspect includes any of the other aspects, wherein the feed stream comprise at least 20 wt. % toluene.

Another aspect includes any of the other aspects, wherein the amount of mesoporous zeolite Beta relative to the total weight of the catalyst mixture is from 40 wt. % to 60 wt. %.

Another aspect includes any of the other aspects, wherein the amount of ZSM-5 zeolite relative to the total weight of the catalyst mixture is from 5 wt. % to 25 wt. %.

Another aspect includes any of the other aspects, wherein the amount of binder material relative to the total weight of the catalyst mixture is from 20 wt. % to 45 wt. %.

Another aspect includes any of the other aspects, wherein the binder material comprises aluminum.

Another aspect includes any of the other aspects, wherein the binder material comprises aluminum in an amount of at least 50 wt. %.

Another aspect includes any of the other aspects, wherein the amount of active metals relative to the total weight of the catalyst mixture is from 1 wt. % to 10 wt. %.

Another aspect includes any of the other aspects, wherein the active metals comprise one or more of molybdenum, platinum, nickel, cobalt, or combinations thereof.

Another aspect includes any of the other aspects, wherein the feed stream is contacted by the catalyst mixture at a temperature of from 50° C. to 600° C.

Another aspect includes any of the other aspects, wherein the feed stream comprises one or more of propylbenzenes, ethylmethylbenzenes, tetramethylbenzenes, ethyldimethylbenzenes, trimethylbenzenes, or diethylbenzenes, methylpropylbenzenes.

Another aspect includes any of the other aspects, wherein: the amount of mesoporous zeolite Beta relative to the total weight of the catalyst mixture is from 40 wt. % to 60 wt. %; the amount of ZSM-5 zeolite relative to the total weight of the catalyst mixture is from 5 wt. % to 25 wt. %; the amount of binder material relative to the total weight of the catalyst mixture is from 20 wt. % to 45 wt. %; the binder material comprises aluminum in an amount of at least 50 wt. %; the amount of active metals relative to the total weight of the catalyst mixture is from 1 wt. % to 10 wt. %; and the active metals comprise one or more of molybdenum, platinum, nickel, cobalt, or combinations thereof.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" a second component, it is contemplated that, in some embodiments, the first component "consists" or "consists essentially of" that second component. It should further be understood that where a first component is described as "comprising" a second component, it is contemplated that, in some embodiments, the first component comprises at least 10%, at least 20%, at least 30%, at least 40%, at least 50%, at least 60%, at least 70%, at least 80%, at least 90%, at least 95%, or even at least 99% that second component (where % can be weight % or molar %).

What is claimed is:

1. A method for producing one or more of benzene, toluene, or xylene, the method comprising:
    contacting a feed stream comprising $C_{9+}$ alkylaromatic hydrocarbons with a catalyst mixture to form one or more of benzene, toluene, or xylene, the catalyst mixture comprising:
        mesoporous zeolite Beta;
        ZSM-5 zeolite;
        one or more active metals; and
        binder material; and
    wherein:
        the feed stream is a heavy reformate and comprises at least 20 wt. % toluene;
        the feed stream comprises $C_{9+}$ alkylaromatic hydrocarbons in an amount of at least 10 wt. %;
        the weight ratio of mesoporous zeolite Beta to ZSM-5 zeolite is from 2 to 4;
        a product stream is formed by the contacting of the feed stream with the catalyst mixture; and
        the product stream comprises less than or equal to 0.5 wt. % ethylbenzene.

2. The method of claim 1, wherein the weight ratio of mesoporous zeolite Beta to ZSM-5 zeolite is from 3 to 4.

3. The method of claim 1, wherein the amount of mesoporous zeolite Beta relative to the total weight of the catalyst mixture is from 40 wt. % to 60 wt. %.

4. The method of claim 1, wherein the amount of ZSM-5 zeolite relative to the total weight of the catalyst mixture is from 5 wt. % to 25 wt. %.

5. The method of claim 1, wherein the amount of binder material relative to the total weight of the catalyst mixture is from 20 wt. % to 45 wt. %.

6. The method of claim 1, wherein the binder material comprises aluminum.

7. The method of claim 1, wherein the binder material comprises aluminum in an amount of at least 50 wt. %.

8. The method of claim 1, wherein the amount of active metals relative to the total weight of the catalyst mixture is from 1 wt. % to 10 wt. %.

9. The method of claim 1, wherein the active metals comprise one or more of molybdenum, platinum, nickel, cobalt, or combinations thereof.

10. The method of claim 1, wherein the feed stream is contacted by the catalyst mixture at a temperature of from 50° C. to 600° C.

11. The method of claim 1, wherein the feed stream comprises one or more of propylbenzenes, ethylmethylbenzenes, tetramethylbenzenes, ethyldimethylbenzenes, trimethylbenzenes, or diethylbenzenes, methylpropylbenzenes.

12. The method of claim 1, wherein:
    the amount of mesoporous zeolite Beta relative to the total weight of the catalyst mixture is from 40 wt. % to 60 wt. %;
    the amount of ZSM-5 zeolite relative to the total weight of the catalyst mixture is from 5 wt. % to 25 wt. %;
    the amount of binder material relative to the total weight of the catalyst mixture is from 20 wt. % to 45 wt. %;
    the binder material comprises aluminum in an amount of at least 50 wt. %;
    the amount of active metals relative to the total weight of the catalyst mixture is from 1 wt. % to 10 wt. %; and
    the active metals comprise one or more of molybdenum, platinum, nickel, cobalt, or combinations thereof.

* * * * *